US008388651B2

(12) United States Patent
Maaskamp et al.

(10) Patent No.: US 8,388,651 B2
(45) Date of Patent: Mar. 5, 2013

(54) APPARATUS AND METHOD FOR DRIVING A HEMORRHAGE OCCLUDER PIN INTO A HUMAN SACRUM

(75) Inventors: Armand Maaskamp, Coto De Casa, CA (US); Asim Syed, Irvine, CA (US)

(73) Assignee: Surgin Surgical Instrumentation, Inc., Irvine, CA (US)

( * ) Notice: Subject to any disclaimer, the term of this patent is extended or adjusted under 35 U.S.C. 154(b) by 0 days.

(21) Appl. No.: 13/399,810

(22) Filed: Feb. 17, 2012

(65) Prior Publication Data

US 2012/0158046 A1 Jun. 21, 2012

Related U.S. Application Data

(63) Continuation of application No. 12/238,710, filed on Sep. 26, 2008, now abandoned.

(51) Int. Cl.
*A61B 17/08* (2006.01)
(52) U.S. Cl. ...................................................... 606/213
(58) Field of Classification Search .................. 411/455
See application file for complete search history.

(56) References Cited

U.S. PATENT DOCUMENTS

| 2,372,930 A | 4/1945 | Bovee |
| 2,483,379 A | 9/1949 | Brell |
| 2,802,211 A | 8/1957 | Friedman |
| 3,470,600 A | 10/1969 | Hosbach |
| 4,061,225 A | 12/1977 | Pettitt |
| 4,631,985 A | 12/1986 | Roberts |
| 4,712,550 A | 12/1987 | Sinnett |
| 4,784,138 A | 11/1988 | Sinnett |
| 4,895,148 A | 1/1990 | Bays et al. |
| 5,464,421 A | 11/1995 | Wortrich |
| 5,492,452 A | 2/1996 | Kirsch et al. |
| 5,921,456 A | 7/1999 | Kirsch et al. |
| 6,575,998 B2 | 6/2003 | Beyar |
| 6,648,203 B2 | 11/2003 | Lord |

OTHER PUBLICATIONS

Wang Qunyao, M.D., S. Weijin, M.D., Z. Youren, M.D., Z. Wenqing, M.D. and H. Zhengrui, "New Concepts in Severe Presacral Hemorrhage During Proctectomy", Arch. Surg (1985), vol. 120; pp. 1013-1020.
S. Nivatvongs, M.D. and D. T. Fang, M.D., "The Use of Thumbtacks to Stop Massive Presacral Hemorrhage", Dis. Col. & Rect. (Sep. 1986), pp. 589-590.
Vito M. Stolfi, M.D., Jeffrey W. Milsom, M.D., I.C. Lavery, M.D., John R. Oakley, M.D., James M. Church, M.D., Victor W. Fazio, M.D., "Newly Designed Occluder Pin for Presacral Hemorrhage," presented at the meeting of the American Soc. Colon & Rectal Surgeons, Boston, Mass, May 12-17, 1991.

*Primary Examiner* — Melanie Tyson
*Assistant Examiner* — Son Dang
(74) *Attorney, Agent, or Firm* — Joshua C. Harrison, Esq.; Barcelo, Harrison & Walker, LLP

(57) ABSTRACT

A method and apparatus to terminate sacral hemorrhaging in a patient having a sacrum and a pubic bone is disclosed. A C-shaped driver is positioned around the pubic bone of the patient and a hemorrhage occluder pin is driven into the sacrum of the patient by applying an impact force to a proximal end of the C-shaped driver. The driver may include a C-shaped shaft that defines a radius in the range 50 mm to 200 mm and a maximum span in the range 100 mm to 650 mm. The proximal end of the C-shaped shaft may have a blunt face with a breadth that is at least 2.5 times the diameter of the pin cap. A shaft distal end has a driver face facing away from an interior of the C-shape, and defining a driver face diameter that is preferably no less than 50% of the pin cap diameter.

13 Claims, 8 Drawing Sheets

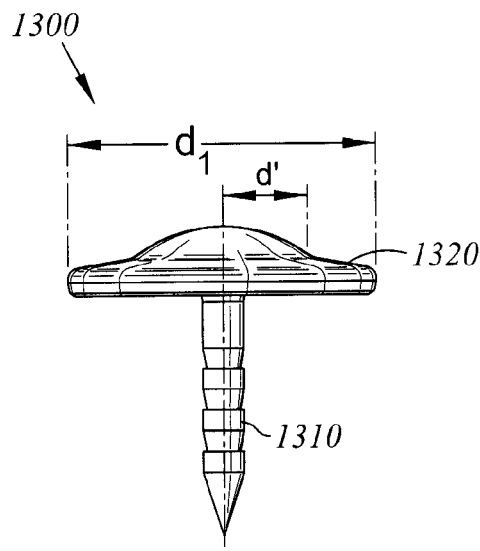
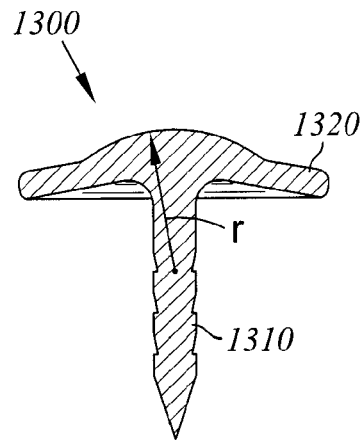
*Fig. 13A*     *Fig. 13B*
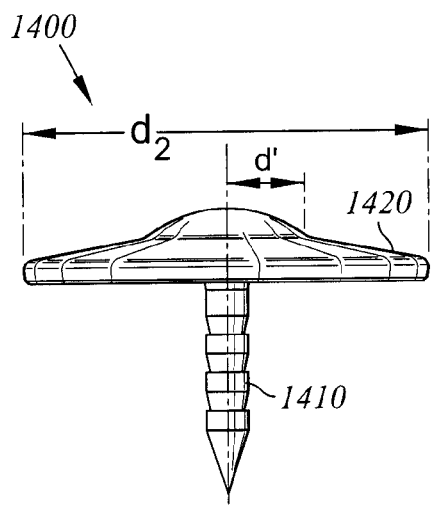
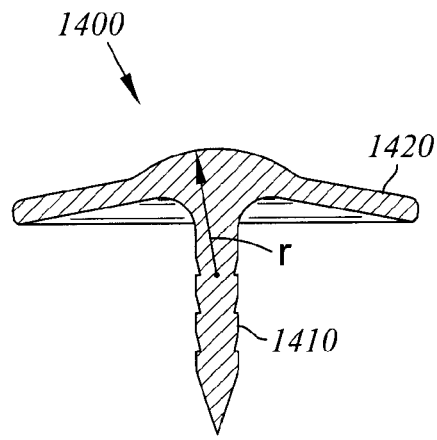
*Fig. 14A*     *Fig. 14B*

APPARATUS AND METHOD FOR DRIVING A HEMORRHAGE OCCLUDER PIN INTO A HUMAN SACRUM

CROSS-REFERENCE TO RELATED APPLICATION

This application claims the benefit under 35 U.S.C. §120 as a continuation of pending U.S. patent application Ser. No. 12/238,710, entitled "APPARATUS AND METHOD FOR DRIVING A HEMORRHAGE OCCLUDER PIN INTO A HUMAN SACRUM," filed on Sep. 26, 2008, which is incorporated herein by reference in its entirety.

FIELD OF THE INVENTION

The present invention relates generally to devices and methods for terminating hemorrhaging in colorectal surgery, and more particularly to devices and methods for terminating bleeding in the presacral venous plexus and the sacral basivertebral veins during surgery.

BACKGROUND

In colorectal surgery, certain incidents can give rise to massive bleeding that cannot conveniently be terminated by suturing or cauterizing. If the presacral fascia is inadvertently entered during rectal surgery, bleeding from the presacral venous plexus and the sacral basivertebral veins may occur. Due to the high density of blood vessels and high volume of blood flow in the region, inadvertent tissue damage may result in severe blood loss which may lead to death in some cases. The urgency of the surgical procedure and the inaccessibility of the hemorrhaging site, as well as the severity of the bleeding, require that hemostatic measures of an unusual kind promptly be undertaken, as commonly used techniques such as packing the site or cauterizing the area often prove ineffective. It is known to terminate the bleeding by occluding or tamponading the vein, using a sterilized pin in the general form of a thumbtack and inserting it into the sacral vertebrae, in such a position that the pin itself or the head of the pin closes the vein. More than one bleeding site must often be occluded during these surgeries.

While this procedure has been used for a number of years, it is accompanied by a number of problems pertaining to difficulties of inserting the occluder pin. Ideally the hemorrhage occluder pin should be inserted fully so that the head of the pin rests on the fascia or bone. However, depending on the location of the bleeder, the curvature of the patient's sacrum, the configuration of the patient's pubic bone, and the hand strength of the surgeon, the pin may not be inserted fully or easily within the close confinement of the working area. On the other hand, full insertion is important to ensure that the bleeding vessels will remain occluded during critical phases of healing and that an abnormal movement, jarring or trauma will not later dislodge the hemorrhage occluder pin.

Even if the surgeon has the necessary hand strength and access to insert the pin fully by hand, the forces involved may increase the chances of tearing or lacerating the surgeon's gloves and skin, exposing the surgeon to the risk of blood-transmitted diseases, such as hepatitis or acquired immune deficiency syndrome. The surgeon might try to protect his hand or increase the insertion force with a foreign body, such as a conventional surgical clamp, but such a conventional tool is not shaped to conveniently access the bleeding site, or be positioned in the proper relationship to the pin.

Therefore, complete, certain, and safe insertion of the pin, regardless of access problems and variation in surgeon hand strength, often may not be achievable by existing devices and procedures, and so there is a need in the art for an improved apparatus and/or method for driving a hemorrhage occluder pin into a human sacrum.

SUMMARY

A method and apparatus to terminate sacral hemorrhaging in a patient having a sacrum and a pubic bone, using a driver for driving a hemorrhage occluder pin having a pin cap into a human sacrum, is disclosed and claimed. The driver may include a C-shaped shaft that defines a radius in the range 50 mm to 200 mm and a maximum span in the range 100 mm to 650 mm. A proximal end of the C-shaped shaft has a blunt face for receiving an impact force, the blunt face having a breadth that may be at least 2.5 times the diameter of the pin cap. A shaft distal end has a driver face that may define a driver face diameter that is no less than 50% of the pin cap diameter, with the driver face facing away from an interior of the C-shape. The hemorrhage occluder pin may be temporarily attached to an applicator. A malleable handle of the applicator may be deformed to position the hemorrhage occluder pin over the sacrum of the patient. The C-shaped driver may be positioned around the pubic bone of the patient so that a concave face of a distal end of the C-shaped driver is adjacent the pin cap, and then the hemorrhage occluder pin may be driven into the sacrum of the patient by applying an impact force to a proximal end of the C-shaped driver.

BRIEF DESCRIPTION OF THE DRAWINGS

FIG. 13A is a side view of a hemorrhage occluder pin capable of use with an embodiment of the present invention.

FIG. 13B is a side cross-sectional view of a hemorrhage occluder pin capable of use with an embodiment of the present invention.

FIG. 14A is a side view of a hemorrhage occluder pin capable of use with an embodiment of the present invention.

FIG. 14B is a side cross-sectional view of a hemorrhage occluder pin capable of use with an embodiment of the present invention.

DETAILED DESCRIPTION

Figure 1:
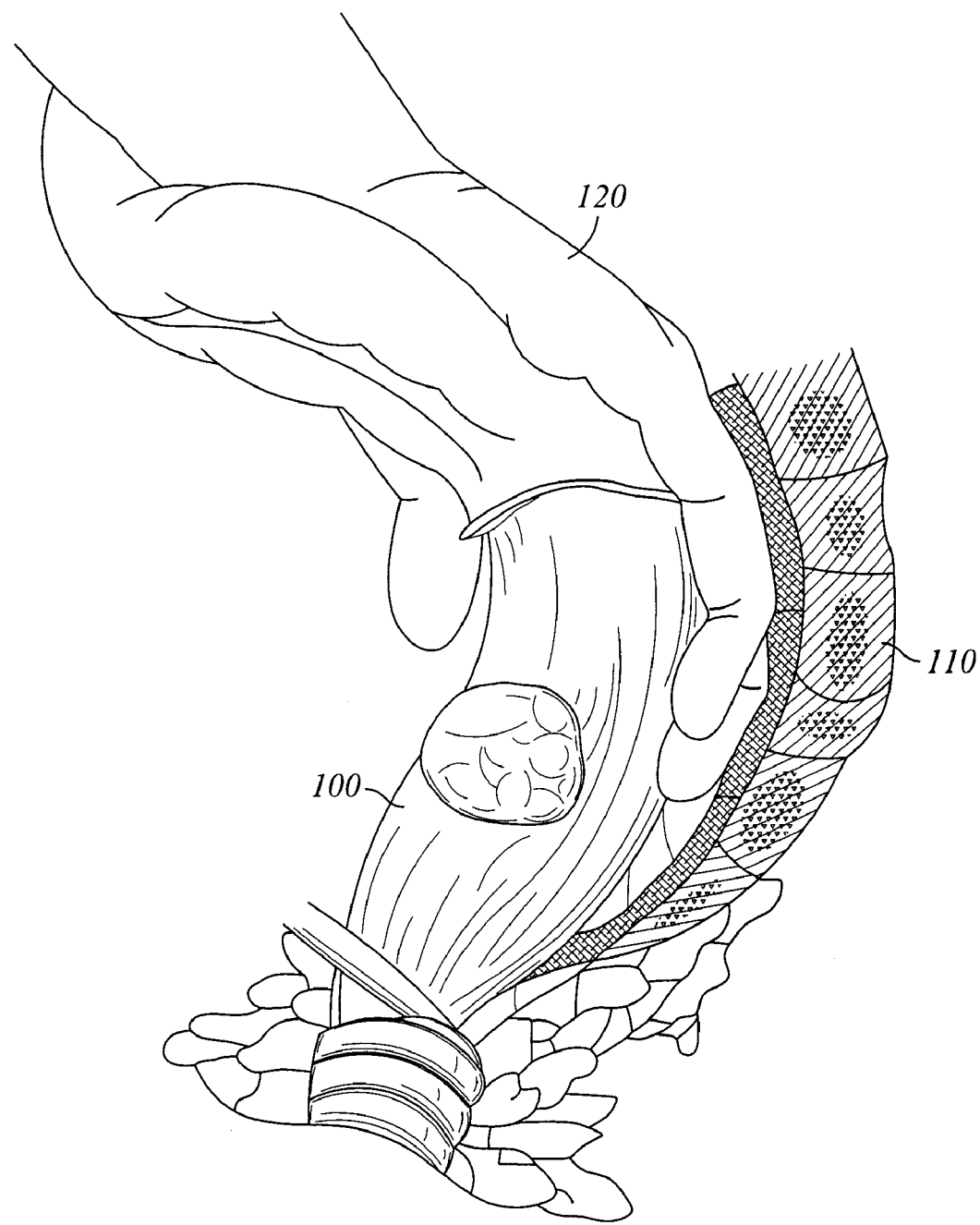
FIG. 1 depicts prior art separation of the rectum from the sacrum by a surgeon's hand during colorectal surgery.

FIG. 1 depicts prior art mobilization of the rectum 100 from its attachments to the sacrum 110 by a surgeon's hand 120 during colorectal surgery. Such mobilization will typically expose the presacral venous plexus, which lies posterior to the fascia propria of the rectum and just below the presacral fascia. Depending on the performance of the surgery, and on the anatomical specifics of the patient, the mobilization may result in considerable bleeding from the presacral venous plexus and the basivertebral veins, through a so-called presacral bleeder, that can continue unless surgically terminated. Such bleeding may be terminated by insertion of a so-called hemorrhage occluder pin into the presacral bleeder through which the bleeding occurs.

Figure 2:
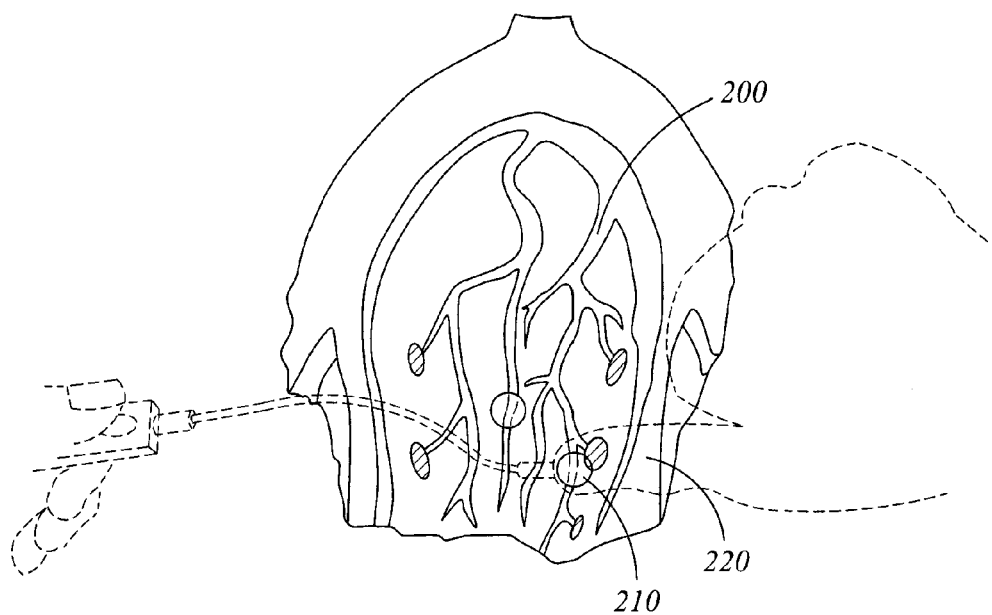
FIG. 2 depicts a prior art method of driving of a hemorrhage occluder pin into a presacral bleeder by a surgeon's thumb.
Figure 3:
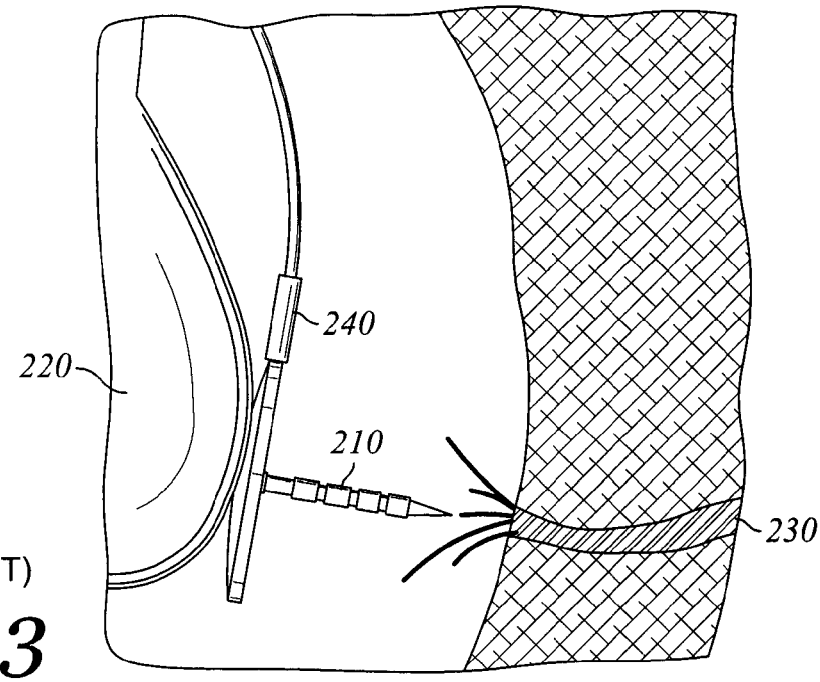
FIG. 3 is a close-up view of a prior art method of driving of a hemorrhage occluder pin into a presacral bleeder by a surgeon's thumb, at a time just before the pin is driven.
Figure 4:
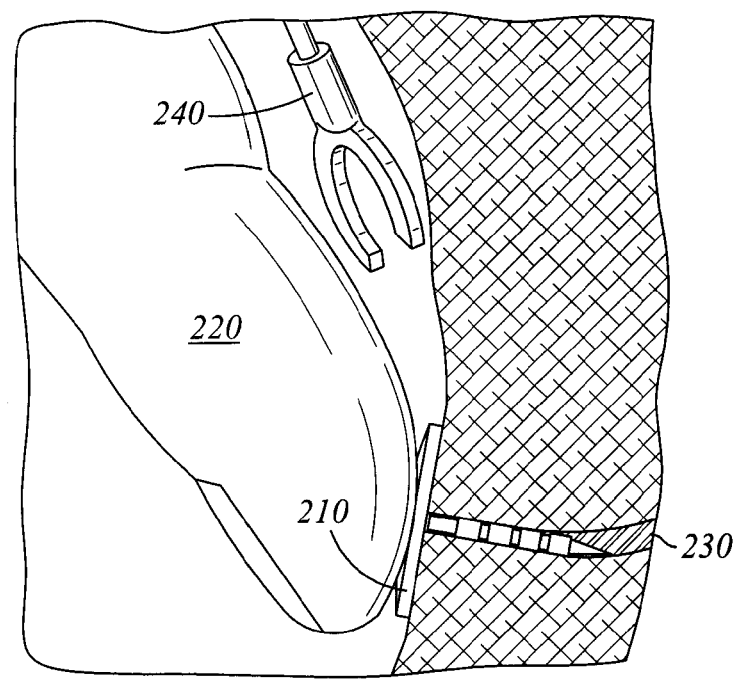
FIG. 4 is a close-up view of a prior art method of driving of a hemorrhage occluder pin into a presacral bleeder by a surgeon's thumb, at a time just after the pin is driven.

FIG. 2 depicts a prior art method of driving a hemorrhage occluder pin 210 into a presacral bleeder in the presacral venous plexus 200 by a surgeon's thumb 220. In the close up view of FIG. 3, the hemorrhage occluder pin 210 is shown just before being driven into the presacral bleeder 230 by the surgeon's thumb 220. FIG. 3 shows that the hemorrhage occluder pin 210 is positioned by the applicator 240. In the close up view of FIG. 4, the hemorrhage occluder pin 210 is shown just after being driven into the presacral bleeder 230 by the surgeon's thumb 220. In FIG. 4, the hemorrhage occluder pin 210 has already been separated from the applicator 240, and the applicator 240 is being removed from the surgical area.

Figure 5:
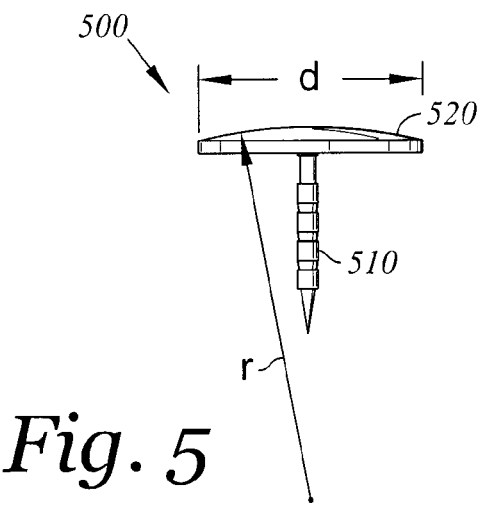
FIG. 5 is a side view of a hemorrhage occluder pin capable of use with an embodiment of the present invention.

FIG. 5 is a side view of a hemorrhage occluder pin 500 capable of use with an embodiment of the present invention. Hemorrhage occluder pin 500 has a pin shank 510 and a pin cap 520 having a pin cap diameter d. As shown in FIG. 5, the pin cap 520 may include a convex upper surface that is contacted when the hemorrhage occluder pin 500 is driven, and that defines a convex radius of curvature r (hereinafter referred to as "convexity"). Although the convexity of the upper surface is not necessary, it is preferable so that the edges of the pin cap 520 may be thinner, and therefore the pin cap 520 may have a lower profile relative to the surface of the sacrum after the pin shank 510 is driven into the sacrum.

Figure 6:
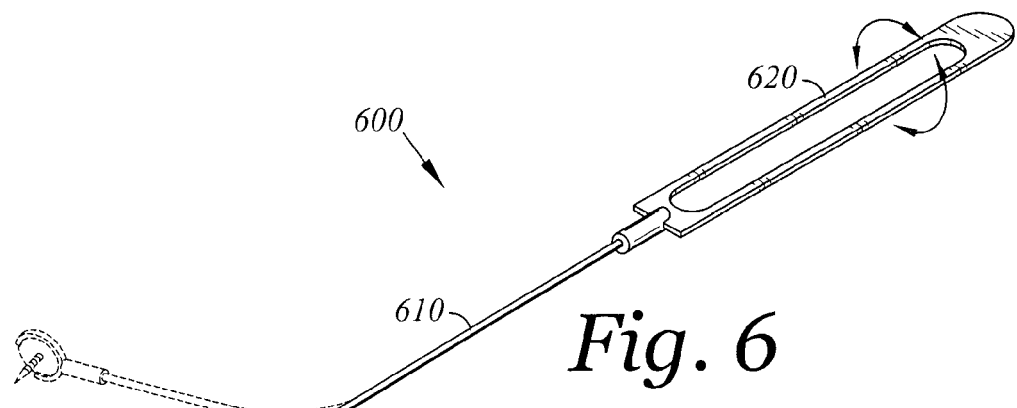
FIG. 6 is a perspective view of a hemorrhage occluder pin applicator capable of being used with an embodiment of the present invention.
Figure 7:
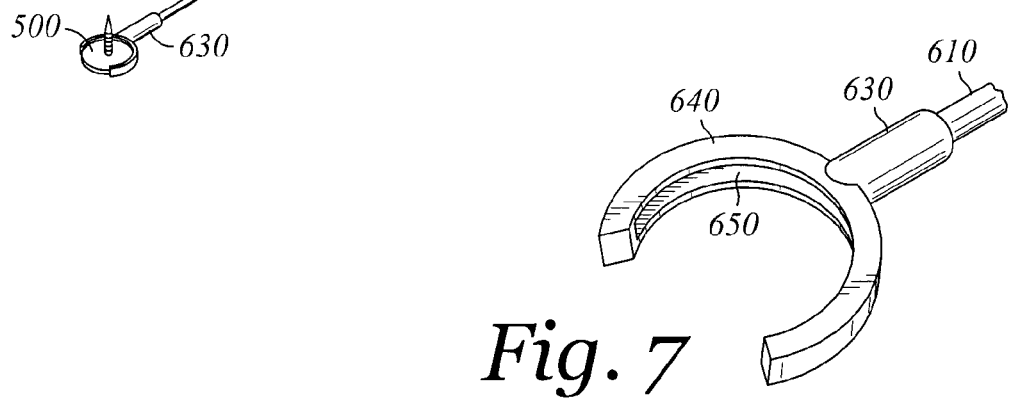
FIG. 7 is a close-up perspective view of a distal end of the hemorrhage occluder pin applicator of FIG. 6.

FIG. 6 is a perspective view of a hemorrhage occluder pin applicator 600 capable of being used with an embodiment of the present invention. The hemorrhage occluder pin applicator 600 includes a handle 620 that is attached on an extender shaft 610. The extender shaft 610 is malleable to accommodate intentional deformations of its shape as desired by the surgeon. For example, the extender shaft 610 may be deformed into a shape like that shown in phantom lines in FIG. 6, among other shapes. The hemorrhage occluder pin applicator 600 also includes pin cap holder 630 attached to a distal end of the extender shaft 610, and in the view of FIG. 6 the pin cap holder 630 is holding a hemorrhage occluder pin 500 by its pin cap. FIG. 7 is a close-up perspective view of the distal end of the extender shaft 610 of the hemorrhage occluder pin applicator 600 of FIG. 6, showing that the pin cap holder 630 may include a C-shaped yoke 640 having a cavity 650 for receiving and temporarily holding an edge of the pin cap of the hemorrhage occluder pin 500.

Other methods of temporary attachment of the hemorrhage occluder pin 500 to the distal end of the extender shaft 610 are also contemplated. For example, an adhesive strip may be attached to the distal end of the extender shaft 610, with the pin cap temporarily adhered thereto (or permanently adhered thereto if the adhesive strip separates from the extender shaft 610 during use and remains in the body of the patient). Also for example, a sheet may be attached to the distal end of the extender shaft, and the pin shank of the hemorrhage occluder pin 500 may pierce through such sheet, so that the hemorrhage occluder pin 500 is thereby attached to the distal end of the extender shaft 610. In such a design, after the hemorrhage occluder pin 500 is inserted or partially inserted in the sacrum the sheet may be pulled away with the pin shank tearing laterally through the sheet to an edge thereof, or alternatively the sheet may tear intentionally along perforations therein and remain in the patient's body as a gasket layer between the underside of the pin cap and underlying tissue (e.g. the sacrum and/or presacral fascia).

Figure 8:
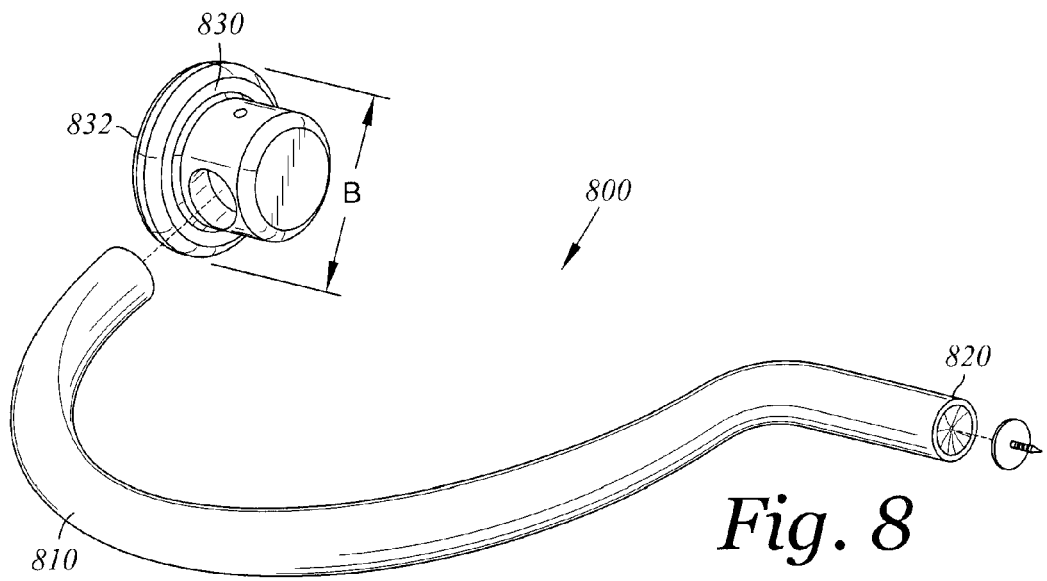
FIG. 8 is an exploded perspective view of a driver for driving a hemorrhage occluder pin, according to an embodiment of the present invention.
Figure 10:
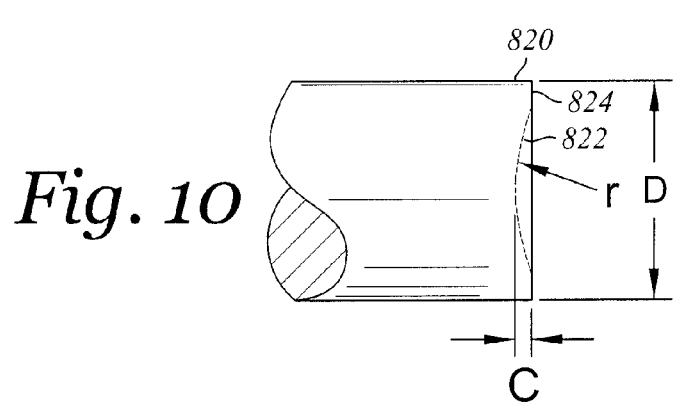
FIG. 10 is a close-up side view of a shaft distal end of a driver for driving a hemorrhage occluder pin, according to an embodiment of the present invention.
Figure 9:
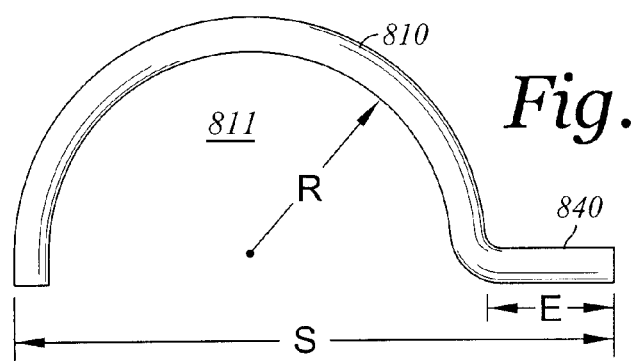
FIG. 9 is a side view of a C-shaped shaft of a driver for driving a hemorrhage occluder pin, according to an embodiment of the present invention.

FIG. 8 is an exploded perspective view of a driver 800 for driving a hemorrhage occluder pin, according to an embodiment of the present invention. FIG. 9 is a perspective view of a C-shaped shaft 810 of the driver 800. FIG. 10 is a close-up side view of a shaft distal end 820 of the driver 800. Now referring to the embodiment of FIGS. 8-10, C-shaped shaft 810 defines a radius R in the range 50 mm to 200 mm and a maximum span S in the range 100 mm to 650 mm. Also in the embodiment of FIGS. 8-10, the C-shaped shaft 810 includes a straight portion 840 defining a straight portion length E in the range 12 mm to 150 mm. These dimensions of the C-shaped shaft 810 may advantageously facilitate positioning of the shaft distal end 820 around the pubic bone in a substantial percentage of patients, depending on the anatomy specific to each of those patients and the location of each patient's presacral bleeder. The C-shaped shaft 810 may be fabricated from stainless steel or titanium, for example.

The C-shaped shaft 810 includes a proximal end 830. The proximal end 830 has a blunt face 832 with a breadth B that is at least 2.5 times the pin cap diameter. Preferably, the blunt face 832 defines a surface area that is at least three times a cross-sectional area of the C-shaped shaft 810. Such breadth or surface area may facilitate the surgeon's transfer of adequate force to the driver 800 without pain or injury to the surgeon's hand. Preferably but not necessarily, the proximal end 830 is rotably attached to the C-shaped shaft 810.

The shaft distal end 820 defines a driver face diameter D that is no less than 50% of the pin cap diameter d. For example, the driver face diameter D may be in the range 5 mm to 20 mm. Such a driver face diameter D may facilitate the stability and control of contact between the driver face of the shaft distal end 820, and the pin cap of the hemorrhage occluder pin, as desired during colorectal surgery. As shown in FIGS. 8-10, both the blunt face 832, and the driver face of the shaft distal end 820, face outward and away from the interior 811 of the C-shape of the C-shaped shaft 810. As shown in FIGS. 8-10, neither the blunt face 832, nor the driver face of the shaft distal end 820, faces into or towards the interior 811 of the C-shape of the C-shaped shaft 810.

In certain embodiments, the shaft distal end 820 is magnetized, which is an optional feature that may be useful in situations where the hemorrhage occluder pin includes a ferromagnetic material. In the embodiment of FIGS. 8-10, the shaft distal end 820 is preferably but not necessarily integral and monolithic with the C-shaped shaft 810 rather than being a sub-component attached to the C-shaped shaft 810.

Also in the embodiment of FIGS. 8-10, the driver face of the shaft distal end 820 preferably but not necessarily includes a concave surface 822 defining a concave radius of curvature r (hereinafter referred to as "concavity") and a concave recession depth C in the range 0.4 mm to 3.2 mm. Preferably, the concavity of the concave surface 822 is approximately equal to the convexity of the upper surface of the pin cap (e.g. pin cap 520). The concave surface 822 may receive at least a portion of the convex upper surface of the pin cap (e.g. pin cap 520), to facilitate some angular variation in the driving angle of the driver 800, while helping to keep the shaft distal end 820 from translating excessively relative to the pin cap. In the embodiment of FIGS. 8-10, the driver face of the shaft distal end 820 also includes an optional annular flat surface 824 surrounding the concave surface 822. The annular flat surface 824 may help facilitate the use of the driver 800 to drive hemorrhage occluder pins that have a flat upper pin cap surface rather than a convex upper pin cap surface.

In certain embodiments, the convex surface of the pin cap may include a central flat spot, for example to facilitate being driven by a shaft distal end that has a flat driver face instead of a concave driver face. However, since the driver face of the shaft distal end 820 of the embodiment of FIGS. 8-10 does not include any central flat spot, a finite clearance would exist between any central flat spot of the pin cap and the concave surface 822, even when the convex surface of the pin cap is in contact with the concave surface 822. Also, the outer edge of the driver face of the shaft distal end 820 may be rounded, although such rounding is not apparent in FIGS. 8-10. Preferably such rounding results in an outer edge radius of curvature that is no less than 0.5 mm. In certain situations, such rounding may advantageously reduce unnecessary tissue damage caused by the outside of the shaft distal end 820.

Figure 11:
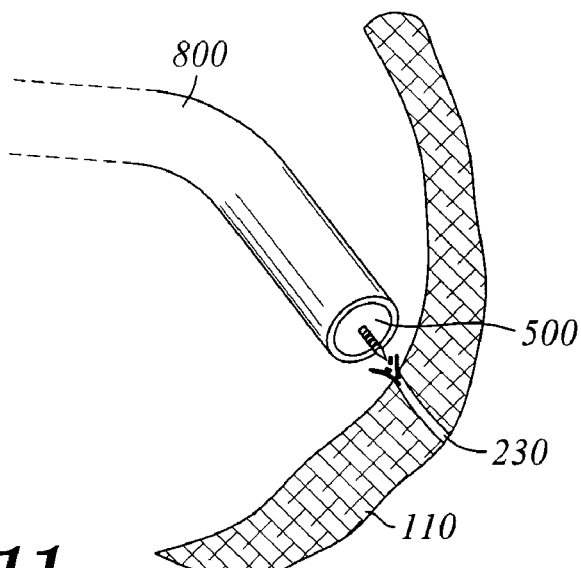
FIG. 11 depicts the use of a driver for driving a hemorrhage occluder pin, according to an embodiment of the present invention, just before driving a hemorrhage occluder pin into a human sacrum.
Figure 12:
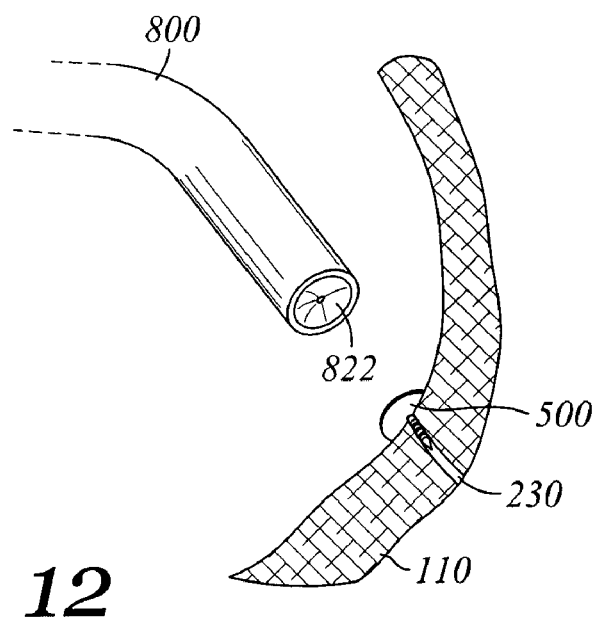
FIG. 12 depicts the use of a driver for driving a hemorrhage occluder pin, according to an embodiment of the present invention, just after driving a hemorrhage occluder pin into a human sacrum.

The driver 800 may be advantageously used to drive a hemorrhage occluder pin into a human sacrum, for example by the following method. The hemorrhage occluder pin may be temporarily attached to an applicator, for example to the applicator 600 shown in FIG. 6. A malleable shaft or handle of the applicator may then be deformed to position the hemorrhage occluder pin over the sacrum of the patient. The driver 800 may be positioned around the pubic bone of the patient so that the distal end of the C-shaped driver is adjacent the pin cap of the hemorrhage occluder pin. FIG. 11 depicts the driver 800 just before driving a hemorrhage occluder pin 500 into a human sacrum 110. Next the driver 800 is used to drive the hemorrhage occluder pin into the sacrum of the patient by applying an impact force to a proximal end of the C-shaped driver. The pin shank of the hemorrhage occluder pin 500 is preferably but not necessarily driven directly into the presacral bleeder 230. FIG. 12 depicts the driver 800 just after driving the hemorrhage occluder pin 500 into the human sacrum 110 at the location of presacral bleeder 230.

Alternatively, the pin shank of the hemorrhage occluder pin may be driven into the human sacrum 110 near or adjacent to the presacral bleeder 230, which may adequately terminate bleeding depending upon the diameter of the pin cap and the pin shank, and the proximity of the pin shank to the presacral bleeder. For example, driving the hemorrhage occluder pin into the human sacrum in a position other than into the presacral bleeder (e.g. near but not at the presacral bleeder) may in many patients require such force as to be greatly facilitated by the use of the driver 800.

In an alternative method, the surgeon may partially drive the hemorrhage occluder pin 500 into the sacrum of the patient by hand and then remove the applicator (e.g. applicator 600) from the hemorrhage occluder pin 500 (e.g. by removing the applicator 600 from the pin cap). The surgeon would then position the driver 800 around the pubic bone of the patient (if necessary) so that the distal end of the driver 800 is adjacent the pin cap. Next, the hemorrhage occluder pin is driven fully into the sacrum of the patient by the surgeon applying an impact force to a proximal end (e.g. proximal end 830) of the driver 800.

FIG. 13A is a side view of a hemorrhage occluder pin 1300 capable of use with an embodiment of the present invention. FIG. 13B is a side cross-sectional view of the hemorrhage occluder pin 1300. Hemorrhage occluder pin 1300 has a pin shank 1310 and a pin cap 1320 having a pin cap diameter $d_1$. As shown in FIGS. 13A and 13B, the pin cap 1320 may include a convex upper surface region of diameter $d'<d_1$, that is contacted when the hemorrhage occluder pin 1300 is driven, and that defines a convexity r.

FIG. 14A is a side view of a hemorrhage occluder pin 1400 capable of use with an embodiment of the present invention. FIG. 14B is a side cross-sectional view of the hemorrhage occluder pin 1400. Hemorrhage occluder pin 1400 has a pin shank 1410 and a pin cap 1420 having a pin cap diameter $d_2>d_1$. As shown in FIGS. 14A and 14B, the pin cap 1420 may include a convex upper surface region of diameter $d'<d_1<d_2$, that is contacted when the hemorrhage occluder pin 1400 is driven, and that defines a convexity r.

Note that although pin cap 1420 has a greater outer diameter $d_2$ than pin cap 1320, the concavity r and the diameter d' of its convex upper surface region may be the same so that the larger hemorrhage occluder pin 1400 may be conveniently driven by the same driver (e.g. driver 800) as the smaller hemorrhage occluder pin 1300.

Figure 15:
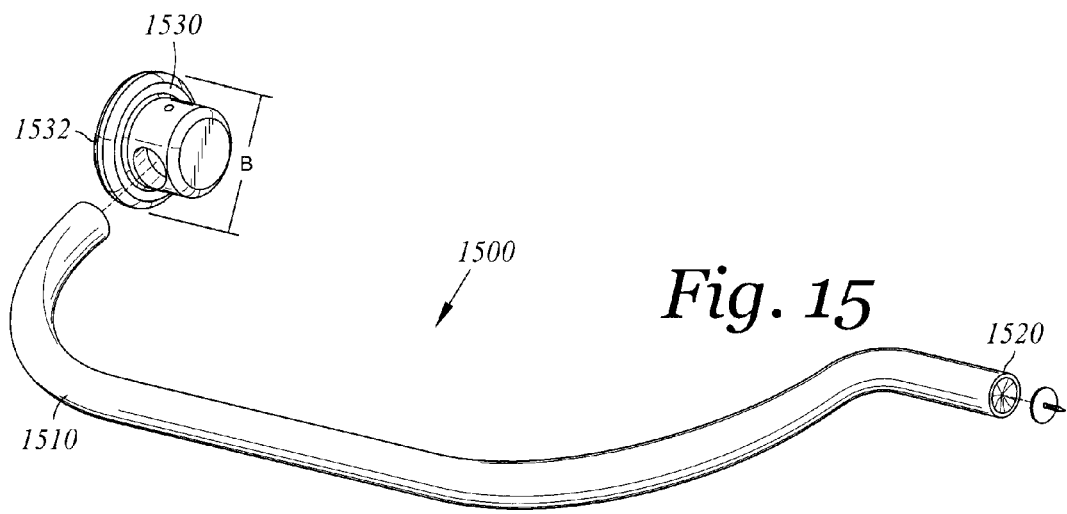
FIG. 15 is an exploded perspective view of a driver for driving a hemorrhage occluder pin, according to an embodiment of the present invention.
Figure 17:
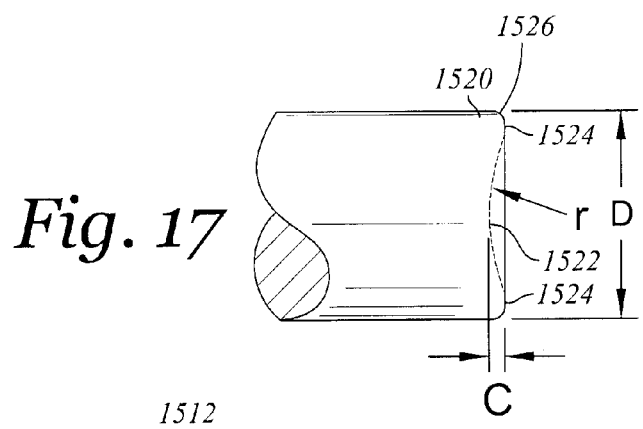
FIG. 17 is a close-up side view of a shaft distal end of a driver for driving a hemorrhage occluder pin, according to an embodiment of the present invention.
Figure 16:
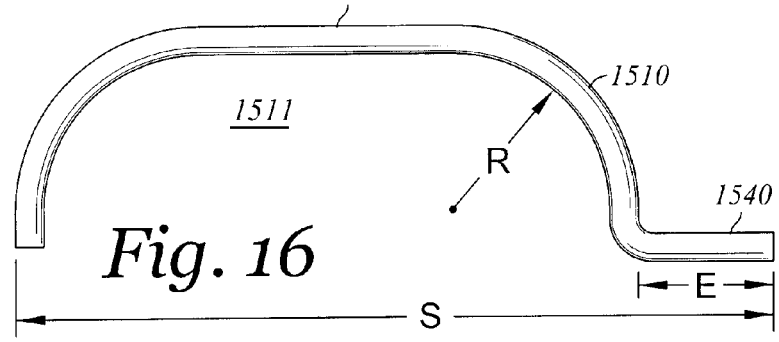
FIG. 16 is a side view of a C-shaped shaft of a driver for driving a hemorrhage occluder pin, according to an embodiment of the present invention.

FIG. 15 is an exploded perspective view of a driver 1500 for driving a hemorrhage occluder pin, according to an embodiment of the present invention. FIG. 16 is a side view of a C-shaped shaft 1510 of the driver 1500. FIG. 17 is a close-up side view of a shaft distal end 1520 of the driver 1500. Now referring to the embodiment of FIGS. 15-17, C-shaped shaft 1510 defines a radius R in the range 50 mm to 200 mm and a maximum span S in the range 100 mm to 650 mm. Also in the embodiment of FIGS. 15-17, the C-shaped shaft 1510 includes two straight portions: a straight portion 1512 in the middle of the C shape (to effectively lengthen the "C"), and a more distal straight portion 1540 defining a straight portion length E in the range 12 mm to 150 mm. These dimensions of the C-shaped shaft 1510 may advantageously facilitate positioning of the shaft distal end 1520 around the pubic bone in a substantial percentage of patients, depending on the anatomy specific to each of those patients and the location of each patient's presacral bleeder. The C-shaped shaft 1510 may be fabricated from stainless steel or titanium, for example.

The C-shaped shaft 1510 includes a proximal end 1530. The proximal end 1530 has a blunt face 1532 with a breadth B that is at least 2.5 times the pin cap diameter d. Preferably, the blunt face 1532 defines a surface area that is at least three times a cross-sectional area of the C-shaped shaft 1510. Such breadth or surface area may facilitate the surgeon's transfer of adequate force to the driver 1500 without pain or injury to the surgeon's hand. Preferably but not necessarily, the proximal end 1530 is rotably attached to the C-shaped shaft 1510.

The shaft distal end 1520 defines a driver face diameter D that is no less than 50% of the pin cap diameter d. For example, the driver face diameter D may be in the range 5 mm to 20 mm. Such a driver face diameter D may facilitate the stability and control of contact between the driver face of the shaft distal end 1520, and the pin cap of the hemorrhage occluder pin, as desired during colorectal surgery. In certain embodiments, the shaft distal end 1520 is magnetized, which is an optional feature that may be useful in situations where the hemorrhage occluder pin includes a ferromagnetic material. In the embodiment of FIGS. 15-17, the shaft distal end 1520 is preferably but not necessarily integral and monolithic with the C-shaped shaft 1510 rather than being a sub-component attached to the C-shaped shaft 1510.

Also in the embodiment of FIGS. 15-17, the driver face of the shaft distal end 1520 preferably but not necessarily includes a concave surface 1522 defining a concavity r and a concave recession depth C in the range 0.4 mm to 3.2 mm. Preferably, the concavity of the concave surface 1522 is approximately equal to the convexity of the upper surface of the pin cap (e.g. pin cap 1320). The concave surface 1522 may receive at least a portion of the convex upper surface of the pin cap (e.g. pin cap 1320), to facilitate some angular variation in the driving angle of the driver 1500, while helping to keep the shaft distal end 1520 from translating excessively relative to the pin cap. As shown in FIGS. 15-17, both the blunt face 1532, and the concave surface 1522 of the driver face of the shaft distal end 1520, face outward and away from the interior 1511 of the C-shape of the C-shaped shaft 1510. As shown in FIGS. 15-17, neither the blunt face 1532, nor the concave surface 1522 of the driver face of the shaft distal end 1520, faces into or towards the interior 1511 of the C-shape of the C-shaped shaft 1510.

In the embodiment of FIGS. 15-17, the driver face of the shaft distal end 1520 also includes an optional annular flat surface 1524 surrounding the concave surface 1522. The annular flat surface 1524 may help facilitate the use of the driver 1500 to drive hemorrhage occluder pins that have a flat upper pin cap surface. Also, in the embodiment of FIG. 17, the outer edge 1526 of the driver face of the shaft distal end 1520 is rounded. Preferably such rounding results in an outer edge radius of curvature that is no less than 0.5 mm. In certain situations, such rounding may advantageously reduce unnecessary tissue damage caused by the outside of the shaft distal end 1520.

While the invention has been described with reference to the specific exemplary embodiments thereof, it should be understood by those skilled in the art that various changes may be made and equivalents may be substituted without departing from the true spirit and scope of the invention as defined by the appended claims. It is contemplated that various features and aspects of the invention may be used individually or jointly and possibly in a different environment or application. The specification and drawings are, accordingly, to be regarded as illustrative and exemplary rather than restrictive. "Comprising," "including," and "having," are intended to be open-ended terms.

What is claimed is:

1. A driver for driving a hemorrhage occluder pin having a pin cap into a human sacrum, the pin cap defining a pin cap diameter, the driver comprising:
   a C-shaped shaft having a C-shape defining a radius in the range 50 mm to 200 mm, and defining a maximum span in the range 100 mm to 650 mm, the C-shaped shaft including
      a proximal end having a blunt face for receiving an impact force, the blunt face having a breadth that is at least 2.5 times the pin cap diameter; and
      a shaft distal end having a driver face for contacting and driving the pin cap, the driver face defining a driver face diameter that is no less than 50% of the pin cap diameter,
   wherein the blunt face and the driver face are oriented to face away from an interior of the C-shape.

2. The driver of claim 1 wherein the shaft distal end is integral and monolithic with the C-shaped shaft rather than being a sub-component attached to the C-shaped shaft.

3. The driver of claim 1 wherein the pin cap includes a convex surface defining a convexity, and the driver face includes a concave surface with a concavity that is approximately equal to the convexity of the pin cap.

4. The driver of claim 3 wherein the concave surface of the driver face defines a recession depth in the range 0.4 mm to 3.2 mm.

5. The driver of claim 3 wherein the driver face further comprises an annular flat surface surrounding the concave surface.

6. The driver of claim 3 wherein the driver face further comprises an outer edge that is rounded with an edge radius of curvature that is no less than 0.5 mm.

7. The driver of claim 1 wherein the driver face diameter is in the range 5 mm to 20 mm.

8. The driver of claim 1 wherein the blunt face defines a surface area that is at least three times a cross-sectional area of the C-shaped shaft.

9. The driver of claim 1 wherein the C-shaped shaft comprises a metal selected from the group consisting of stainless steel and titanium.

10. The driver of claim 3 wherein the convex surface of the pin cap includes a central flat spot, and the concave surface of the driver face does not include any central flat spot so that a finite clearance exists between the central flat spot and the concave surface of the driver face even when the convex surface of the pin cap is in contact with the concave surface of the driver face.

11. The driver of claim 1 wherein the shaft distal end is magnetized.

12. The driver of claim 1 wherein the C-shaped shaft further includes a straight portion defining a straight portion length in the range 12 mm to 150 mm.

13. The driver of claim 1 wherein the proximal end is rotably attached to the C-shaped shaft.

* * * * *